(12) United States Patent
Ryu et al.

(10) Patent No.: US 7,932,038 B2
(45) Date of Patent: Apr. 26, 2011

(54) DNA COLLECTION STICKER AND METHOD FOR ISOLATING DNA FROM THE STICKER

(75) Inventors: Jae-Song Ryu, Bucheon-Si (KR); Yong-Kil Yu, Bucheon-Si (KR)

(73) Assignee: Youn-Zoo Jang, Seoul (KR)

( * ) Notice: Subject to any disclaimer, the term of this patent is extended or adjusted under 35 U.S.C. 154(b) by 352 days.

(21) Appl. No.: 12/083,074

(22) PCT Filed: Oct. 5, 2005

(86) PCT No.: PCT/KR2005/003278
§ 371 (c)(1),
(2), (4) Date: Apr. 3, 2008

(87) PCT Pub. No.: WO2007/040287
PCT Pub. Date: Apr. 12, 2007

(65) Prior Publication Data
US 2009/0269743 A1     Oct. 29, 2009

(51) Int. Cl.
*C12Q 1/68*       (2006.01)
*C12M 1/34*       (2006.01)

(52) U.S. Cl. .......................................... 435/6; 435/287.2
(58) Field of Classification Search .................. None
See application file for complete search history.

(56) References Cited

U.S. PATENT DOCUMENTS
6,355,439 B1     3/2002    Chung et al.

FOREIGN PATENT DOCUMENTS
KR     10-2001-0016420     3/2001

*Primary Examiner* — Bradley L Sisson
(74) *Attorney, Agent, or Firm* — Birch, Stewart, Kolasch & Birch, LLP

(57) ABSTRACT

The present invention relates a sticker for DNA collection and a method for isolating DNAs using the same. Particularly, the sticker for DNA collection is covered with a paint solution comprising EDTA, Tris, SDS and peyonine to isolate keratins exclusively when attached onto human skin and detached. Further, the specific sticker for DNA collection separates DNAs efficiently to amplify genes by using a PCR technique. Therefore, the present invention can be applied to identify a real child and investigate a crime with a fingerprint and to screen genetic diseases.

2 Claims, 2 Drawing Sheets

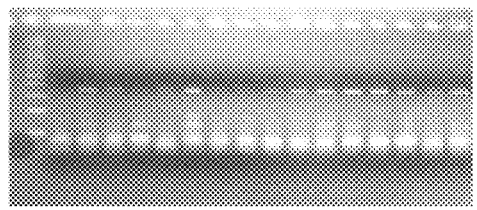
FIG.2A ApoE gene PCR result
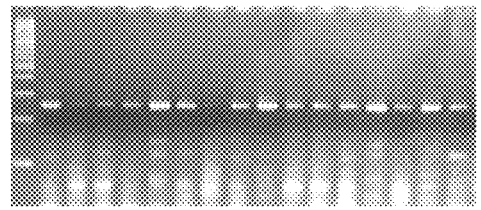
FIG.2B IL4 gene PCR result
FIG.3A ST gene PCR result
FIG.3B DRD2 gene PCR result

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Synthetic primer

<400> SEQUENCE: 1
tcggccgcag ggcgctgatg gac                                    23

<210> SEQ ID NO 2
<211> LENGTH: 22
<212> TYPE: DNA
<213> ORGANISM: Artificial Sequence
<220> FEATURE:
<223> OTHER INFORMATION: Synthetic primer

<400> SEQUENCE: 2
cccaggcgct cgcggatggc gc                                     22

<210> SEQ ID NO 3
<211> LENGTH: 16
```

```
<212> TYPE: DNA
<213> ORGANISM: Artificial Sequence
<220> FEATURE:
<223> OTHER INFORMATION: Synthetic primer

<400> SEQUENCE: 3
gacccaaact aggcct                                                      16

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
cagtcctcct ggggaaagat                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
ggcgttgccg ctctgaatgc                                                  20

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
gagggactga gctggacaac cac                                              23

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
gatgataccc acttcaggaa g                                                21

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
gatgtgtagg aattagccag g                                                21
```

DNA COLLECTION STICKER AND METHOD FOR ISOLATING DNA FROM THE STICKER

TECHNICAL FIELD

The present invention relates to a sticker for DNA collection and a method for extracting DNAs using the same, more particularly to a DNA collection sticker, which conveniently separates keratin attached to human skin without blood or hair to collect a human gene and amplify the gene by using a PCR technique for identifying a real child and investigating a crime, and a method for collecting DNAs efficiently using the same.

BACKGROUND ART

Generally, DNA (deoxyribonucleic acid), a molecule containing genetic information in a human body is stored in 23 pairs of human chromosomes. In respect of genetic information, DNA is composed of exon encoding a protein and intron, a non-coding region. The intron region, especially Alu sequence has a repeated pattern specific for an individual, depending upon its genetic lineage. For this reason, it is being adopted for a gene fingerprint to screen a similar or same sequence scattered onto a genome, i.e. microsatellite or VNTR (Variable Number of Tandem Array).

Presently, in order to collect DNAs from a human body, the method using blood or hair has been disclosed. However, there are several problems. This technique is complicated in the procedure as well as often discomforted.

Further, the sticker for DNA collection has been developed to exploit skin keratin easily fallen apart from a human body. The conventional sticker is problematic, because the keratin containing DNAs is too difficult to be displaced exclusively from the adhesive ingredient on the sticker. In detail, the adhesive may agglomerate with DNAs under a normal condition when separating DNA, because the effective ingredient of adhesive is a polymer like DNA.

Therefore, the present inventors have demonstrated the sticker that is prepared by coating a paint solution comprising EDTA (ethylene diamine tetraacetate), Tris and SDS (sodium dodecyl sulphate) in the Korean Patent Application NO. 2000-74853 (hereinafter, referred to as "conventional invention"). The resulting sticker can collect DNAs exclusively from skin keratin in a human body. Then, the DNA resultant is separated from the sticker by using a phenol extraction method. Unfortunately, this process has not improved the DNA yield satisfactorily, compared to conventional techniques, even though exploiting the sticker and the phenol extraction.

DISCLOSURE

Technical Problem

In order to settle above-mentioned problems, the present inventors have developed the following invention successfully. The object of the present invention is to provide a sticker for DNA collection that improves the productive yield of DNA.

The other object of the present invention is to provide a method for purifying DNA efficiently using the sticker for DNA collection, which improves to conveniently separate keratin attached from human skin to obtain a human gene.

Technical Solution

Precisely, the present invention comprises several steps as follows: (1) preparing a sticker; (2) collecting keratin from human skin; (3) purifying DNAs; (4) amplifying DNA by performing PCR; and (4) identifying various genes and genetic information of individual.

In order to achieve the objects of the present invention, the sticker prepared by coating a paint solution comprising EDTA (ethylene diamine tetraacetate), Tris and SDS (sodium dodecyl sulphate) and Peyonine is attached and detached, before collecting to analyze genes from a human body. Then, the resulting sticker is reacted with the paint solution at 30~45° C. for 40~80 minutes. After that, proteinase K is added and reacted at 40~68° C. for 30~100 minutes.

The method for separating DNA using the sticker for DNA collection of the present invention has a feature to comprise following steps:

i) coating a paint solution comprising 0.05~1 mol of EDTA (pH 8.0), 0.002~0.015 mol of Tris (pH 8.0), 30~40 vol % of SDS (approximately 1~1.4 mol) and 3% Peyonine onto one side of a commercial sticker for human use to prepare a sticker for DNA collection;

ii) attaching the sticker onto human skin and detaching to collect human keratin;

iii) adding a protein precipitation reagent to purify DNA from the resulting keratin;

iv) performing PCR to amplify the resulting DNA;

v) examining the PCR product to identify various genes and genetic information of individual within a DNA specimen.

Hereinafter, the present invention will be described more clearly according to following steps.

Step 1: Preparation of Sticker for DNA Collection

The sticker used in the present invention is a product for human use containing a nontoxic adhesive ingredient and commercially available. The commercial sticker is coated with a paint solution comprising EDTA (ethylene diamine tetraacetate), Tris and SDS (sodium dodecyl sulphate) and Peyonine onto one side containing an adhesive agent to manufacture the sticker for DNA collection.

The paint dose should be adjusted properly. If higher, the sticker for DNA collection is too difficult to attach onto a human body. In contrast, if lower, it is too hard to separate human keratin from adhesive agent. Preferably, the surface for attachment is coated with a paint solution in 70~85% and more preferably, in 75%. Also, the paint thickness should be controlled properly to contact an adhesive agent and a human body. Preferably, the paint thickness is less than 3 mm.

In the paint solution, EDTA plays a role to remove a magnesium ion and weaken the cell membrane because the magnesium is essential to maintain the overall structure of cell membrane; and further, help intact DNAs collected by inhibiting intracellular enzymes. In addition, Tris, a buffering system is nontoxic, cheap and suitable for frequent use. SDS, a sort of detergent plays a role to help a cell lysis by removing lipid molecules and cause the dissociation of cell membrane. In order to prepare the paint solution working properly, 0.05~1 mol of EDTA (pH 8.0) and 5~15 mol of Tris (pH 8.0) are mixed with 3% peyonine and SDS adjusting to 30~40 vol % to reach 7,000~8,0001 ml of total volume by adding distilled water. Preferably, 0.1 mol of EDTA and 10 mols of Tris are mixed with 3% peyonine and SDS adjusting to 37.5 vol % to reach 7,500 ml of total volume by adding distilled water.

Step 2: Collection of Human Keratin

The sticker of the present invention prepared above can be attached onto any region in a human body. Preferably, the sticker can be applied onto a keratinous region such as elbow, axilla, arm, ankle and face. The sticker of the present invention may not affected by a duration period. Right after the attachment, the sticker of the present invention can collect the specimen in a proper amount.

Step 3: Purification of DNAs

From the sticker prepared above, human keratins are collected and then, DNAs are purified as follows.

(i) Above all, an adhesive portion is cut to a proper size (approximately 4 cm×6 cm) from the sticker and immersed in DNA extraction solution having the same composition and ratio with that of the paint solution. This composition and ratio facilitates the dissociation between adhesive ingredients of the sticker and human keratins collected. Thus, the paint solution is dissolved easily toward DNA extraction solution.

The resulting paint solution is incubated under an immersed state at 30° C.~45° C., preferably 30° C. for 40~80 minutes and more preferably, 37° C. for 60 minutes. If incubated at under 30° C., the dissolution ratio of the paint solution decreases. The paint solution between adhesive ingredients of the sticker and human keratins collected is less recovered due to low activities of the DNA extraction solution and the paint solution. As a result, the recovery ratio of DNA decreases to less than 60% and further analyses could not be accomplished. In contrast, if incubated at over 45° C., the adhesive ingredient, polymer substance may be dissolved into the DNA extraction solution from the sticker and decrease the activities of the DNA extraction solution and the paint solution. As a result, the recovery ratio of the adhesive ingredient increases remarkably, compared to that of the human keratins and further DNA analyses as well as PCR amplification could not be accomplished.

In the meantime, if incubated for under 40 minutes, the dissolution period is too short to separate adhesive ingredients of the sticker and human keratins fully. Further DNA analyses and PCR amplification could be hardly accomplished. If incubated for over 80 minutes, the adhesive ingredients of the sticker are dissociated together during a final alcohol extraction in the DNA purification. Further PCR amplification could be hardly accomplished. Accordingly, the incubation should be performed under a proper condition.

(ii) After the incubation, proteinase K, a protein degradation enzyme is added to remove proteins. At this moment, proteinase K is reacted at 40~68° C. for 30~100 minutes and preferably, at 5° C. for 90 minutes. If reacted for over 100 minutes, the recovery amount of DNA decreases due to the action of Dnase after separated together from skin. If reacted for under 30 minutes, proteins are not discarded sufficiently. In contrast, if reacted at under 40° C. or over 68° C., the activity of proteinase K, a protein degradation enzyme sensitive to temperature decreases. The keratins collected form a human body remains agglomerated. Further, the recovery ratio of DNA decreases. Especially, if reacted at over 68° C., DNAs separated above becomes denatured.

(iii) Protein precipitation solution is added in a half volume of the resulting solution and centrifuged to precipitate proteins. The water layer placed in supernatant is separated by using a pipette. After that, isopropanol is added to the resultant in the same volume and again centrifuged to obtain DNA specimen. Then, 70% ethanol is poured to the resulting specimen in the same volume under a salt like sodium ion and centrifuged at −20° C. to precipitate DNAs (DNA concentration).

Step 4: Amplification of DNA by PCR (Polymerase Chain Reaction)

The resulting DNAs is washed by using 70% ethanol, dried and dissolved with TE buffer. The purified DNA can be amplified for a short time by performing PCR (polymerase chain reaction). Also, the DNA collected from the sticker can be amplified by performing the PCR. Through this procedure, DNAs is produced in a sufficient amount even after 2~3 cycles of PCR.

Step 5: Identification of Various Genes and Genetic Information of Individual

The DNA specimen prepared above can be applied to screen various genes and genetic information of individual. Further, the genetic characteristics can be used to identify a real child or investigate a suspected person in a crime. In addition, the DNA collected by this procedure can be utilized to screen genetic diseases as well as to screen such a fingerprint. In detail, Southern blotting and DNA chip using the principle of hybridization between DNAs are accomplished in order to identify various genes and genetic information of individual.

As illustrated above, the sticker for DNA collection and the method for collecting DNA using the same enables keratin attached from human skin separated easily without blood or hair and further human gene separated conveniently and amplified by using a PCR technique. Therefore, the present invention may attain the effect that identifies a real child, investigates a crime and the like.

That is to say, the specific sticker for DNA collection is attached onto skin, detached and applied to separate DNAs efficiently, which facilitates the identification of personal genetic information.

Advantageous Effects

As described above, the sticker for DNA collection and the method for collecting DNA using the same according to the present invention is advantageous in that, enable keratin attached from human skin separated easily without blood or hair. Further, the present invention enables a human gene separated conveniently and amplified by using a PCR technique. Therefore, the present invention may attain the effect that identifies a real child, investigates a crime and the like. Hence, the sticker for DNA collection and the method for collecting DNA using the same are industrially useful in genetic engineering fields.

BRIEF DESCRIPTION OF THE DRAWINGS

The above and other objects, features and other advantages of the present invention will be more clearly understood from the following detailed description taken in conjunction with the accompanying drawings, in which;

FIG. 2 depicts the comparison of productive yields of PCR products prepared by DNAs from the sticker of the present invention and conventional stickers.

FIG. 3 depicts the comparison of PCR products prepared by the DNA separated with a reagent precipitating proteins and through a phenol extraction from the sticker of the present invention.

BEST MODE FOR CARRYING OUT THE INVENTION

Figure 1:
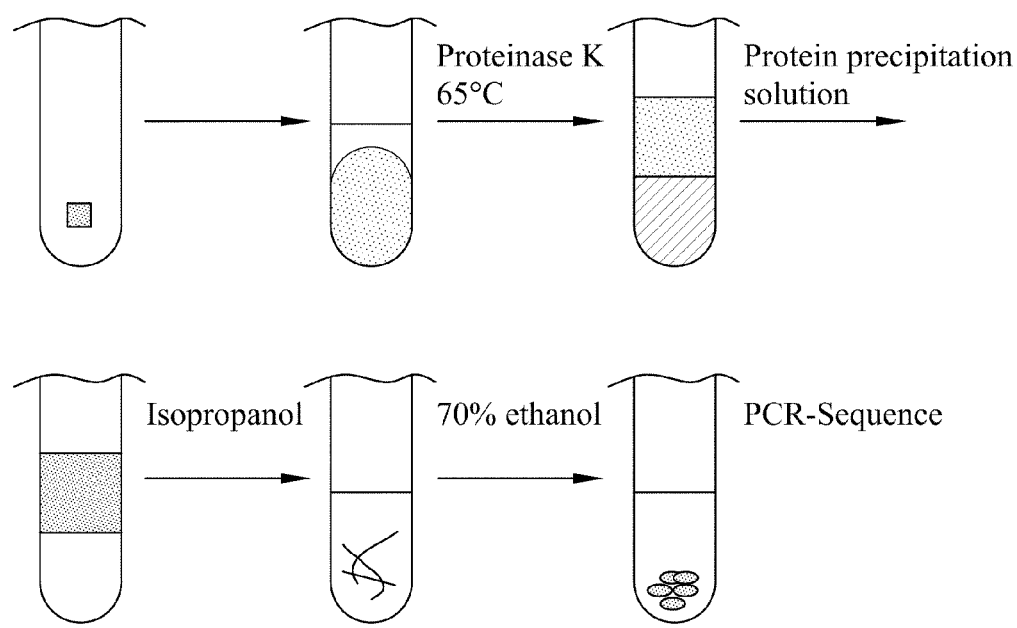
FIG. 1 depicts the schematic diagram of the procedure separating DNAs from a sticker.

Practical and presently preferred embodiments of the present invention are illustrated as shown in the following Examples.

However, it will be appreciated that those skilled in the art, on consideration of this disclosure, may make modifications and improvements within the spirit and scope of the present invention.

EXAMPLE 1

Preparation of Sticker and Collection of Human Keratin

In order to prepare a paint solution, 0.1 mol of EDTA (pH 8.0) and 10 mol of Tris (pH 8.0) were mixed with 3% peyonine and SDS adjusting to 30~40 vol %. Then, the final volume was adjusted to 7,500 ml by adding distilled water. The resulting solution was coated onto one side of stickers for human use that contains an adhesive ingredient nontoxic to a human body to cover 75% of the side area in 2 mm of thickness.

The sticker coated above was attached onto the palm and after 10 minutes, detached again.

Mode of the Invention

EXAMPLE 2

Purification of DNAs from Human Keratin Attached onto Sticker

The sticker prepared in Example 1 was cut to 4 cm×6 cm of square, submerged in a paint solution having the same composition and ratio with those of Example 1 and reacted at 37° C. for 60 minutes. After that, proteinase K, a protein degradation enzyme was added and incubated at 65° C. for 90 minutes.

Then, a protein precipitation solution was added in a half volume of the resulting solution and centrifuged to discard proteins. The water layer placed in supernatant was separated by using only a pipette. After that, isopropanol was added to the resultant in the same volume and again centrifuged to obtain DNA specimen. Then, 70% ethanol was poured to the resulting specimen in the same volume under a salt like sodium ion and centrifuged at −20° C. to precipitate DNAs (DNA concentration).

EXPERIMENTAL EXAMPLE 1

Examination of DNA Amounts Under Various Conditions

The stickers prepared in Example 1 and 2 were analyzed under various conditions, according to the composition of adhesive agent, the temperature and time period of incubation and the reaction period and temperature of proteinase K. The experimental data were illustrated in Tables as follows.

TABLE 1

DNA amounts from human body according to composition of adhesive agent in sticker

| Samples | EDTA (mol) | Tris (mmol) | SDS (vol %) | DNA amount (μg/ml) |
| --- | --- | --- | --- | --- |
| 1 (Control) | 0 | 0 | 0 | 0 |
| 2 (Example 1, 2) | 0.1 | 10 | 37.5 | 45 |
| 3 | 0.05 | 5 | 30 | 39 |
| 4 | 0.1 | 15 | 40 | 40 |

* The DNA amounts were measured by UV absorbance. For reference, if the absorbance is 1 at 260 nm, dsDNA is estimated to 50 μg/ml of concentration.

TABLE 2

DNA amounts from human body according to temperature of incubation in sticker

| Samples | DNA amount collected (μg/ml) |
| --- | --- |
| 1 (Control) | 0 |
| 2 (37° C.) | 45 |
| 3 (30° C.) | 30 |
| 4 (45° C.) | 35 |

* The DNA amounts were measured by UV absorbance. For reference, if the absorbance is 1 at 260 nm, dsDNA is estimated to 50 μg/ml of concentration.

TABLE 3

DNA amounts from human body according to time period of incubation in sticker

| Samples | DNA amount collected (μg/ml) |
| --- | --- |
| 1 (Control) | 0 |
| 2 (60 min) | 45 |
| 3 (40 min) | 30 |
| 4 (80 min) | 35 |

* The DNA amounts were measured by UV absorbance. For reference, if the absorbance is 1 at 260 nm, dsDNA is estimated to 50 μg/ml of concentration.

TABLE 4

DNA amounts from human body according to reaction period of proteinase K (the composition of paint solution is the same with that of Example 1 and 2)

| Samples | DNA amount collected (μg/ml) |
| --- | --- |
| 1 (Control) | 0 |
| 2 (90 min) | 45 |
| 3 (30 min) | 20 |
| 4 (100 min) | 35 |

* The DNA amounts were measured by UV absorbance. For reference, if the absorbance is 1 at 260 nm, dsDNA is estimated to 50 μg/ml of concentration.

TABLE 5

DNA amounts from human body according to reaction temperature of proteinase K (the composition of paint solution is the same with that of Example 1 and 2)

| Samples | DNA amount collected (μg/ml) |
| --- | --- |
| 1 (Control) | 0 |
| 2 (65° C.) | 45 |
| 3 (40° C.) | 29 |
| 4 (68° C.) | 31 |

* The DNA amounts were measured by UV absorbance. For reference, if the absorbance is 1 at 260 nm, dsDNA is estimated to 50 μg/ml of concentration.

EXPERIMENTAL EXAMPLE 2

Comparison of Productive Yields of Human DNAs in the Sticker of the Present Invention and Conventional Stickers In order to compare DNA productive yields of the sticker prepared in Examples and conventional stickers, PCR was performed by using ApoE gene and IL-4 gene.

i) The primer sequences for amplifying ApoE gene were described as follows:

```
                                          (SEQ ID NO: 1)
    Forward:   5'-tcggccgcagggcgctgatggac-3'

(SEQ ID NO: 2)
    Reverse:   5'-cccaggcgctcgcggatggcgc-3'
```

PCR was performed under a following condition.

95° C., 5 min; 95° C., 20 sec, 70° C., 1 min, 40 cycles, 72° C., 1 min; 72° C., 5 min ii) The primer sequences for amplifying IL4 gene were described as follows:

```
                                           (SEQ ID NO: 3)
    Forward:       5'-gacccaaactaggcct-3'

(SEQ ID NO: 4)
    Reverse:       5'-cagtcctcctggggaaagat-3'
```

PCR was performed under a following condition.
95° C., 5 min; 95° C., 30 sec, 62° C., 30 sec, 40 cycles, 72° C., 1 min; 72° C., 5 min As illustrated in FIG. 2, conventional stickers and the sticker of the present invention varying the composition were used to extract DNAs in 8 of target persons. Then, ApoE gene and IL-4 gene were amplified by performing PCR. As a result, it is identified that both data is improved in the sticker of the present invention.

EXPERIMENTAL EXAMPLE 3

Comparison of DNA Productive Yields According to Methods for Separating DNAs from Stickers In order to compare DNA productive yields of the sticker prepared in Examples according to methods for separating DNAs, PCR was performed by using ST gene and DRD2 gene.

i) The primer sequences for amplifying ST gene were described as follows:

```
                                           (SEQ ID NO: 5)
    Forward:    5'-ggcgttgccgctctgaatgc-3'

(SEQ ID NO: 6)
    Reverse:    5'-gagggactgagctggacaaccac-3'
```

PCR was performed under a following condition.
95° C., 5 min; 95° C., 20 sec, 60° C., 40 sec, 40 cycles, 72° C., 1 min; 72° C., 5 min ii) The primer sequences for amplifying DRD2 gene were described as follows:

```
                                           (SEQ ID NO: 7)
    Forward:       5'-gatgatacccacttcaggaag-3'

(SEQ ID NO: 8)
    Reverse:       5'-gatgtgtaggaattagccagg-3'
```

PCR was performed under a following condition.
95° C., 5 min; 95° C., 20 sec, 60° C., 40 sec, 40 cycles, 72° C., 1 min; 72° C., 5 min As illustrated in FIG. 3, the productive yields of DNAs that are extracted with protein precipitation solution through a traditional phenol extraction according to the present invention were compared in 5 of target persons. ST gene and DRD2 gene were amplified by performing PCR. As a result, it is confirmed that both data is improved, when using the extraction method of the present invention.

INDUSTRIAL APPLICABILITY

The sticker for DNA collection and the method for collecting DNA using the same enable keratin attached from human skin separated easily without blood or hair. Further, the present invention enables a human gene separated conveniently and amplified by using a PCR technique. Therefore, the present invention may attain the effect that identifies a real child, investigates a crime and the like. Hence, the sticker for DNA collection and the method for collecting DNA using the same are industrially useful in genetic engineering fields.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

The invention claimed is:

1. A sticker for DNA collection, which is covered onto one side with a paint solution comprising 0.05~1 mol of EDTA (pH 8.0), 0.002~0.015 mol of Tris (pH 8.0), 30~40 vol % of SDS (approximately 1~1.4 mol) and 3% peyonine.

2. A method for collecting DNA using a sticker for DNA collection, which comprises additional steps: (1) obtaining skin keratin from a human body by using the sticker for DNA collection of claim 1; (2) digesting with protease K to separate DNAs from the sticker; and then, (3) adding a reagent to precipitate proteins in a half volume of the resulting solution.

* * * * *